United States Patent [19]

Yamashita et al.

[11] 4,313,735
[45] Feb. 2, 1982

[54] AUTOMATIC CHEMICAL ANALYZING METHOD AND APPARATUS

[75] Inventors: Katsuji Yamashita, Katsuta; Yasushi Nomura, Mito, both of Japan

[73] Assignee: Hitachi, Ltd., Tokyo, Japan

[21] Appl. No.: 180,476

[22] Filed: Aug. 22, 1980

[30] Foreign Application Priority Data

Aug. 22, 1979 [JP] Japan ................................ 54/105904

[51] Int. Cl.$^3$ ...................... G01N 35/04; G01N 35/06
[52] U.S. Cl. .................................. 23/230 R; 364/498; 422/64; 422/65; 422/67
[58] Field of Search ................. 23/230 R; 422/63, 64, 422/65, 67; 364/497, 498

[56] References Cited

U.S. PATENT DOCUMENTS

| | | | |
|---|---|---|---|
| 3,481,709 | 12/1969 | Slone | 422/67 X |
| 3,762,879 | 10/1973 | Moran | 422/65 |
| 3,960,497 | 6/1976 | Acord | 422/67 |
| 4,025,311 | 5/1977 | Bochinski | 422/67 |
| 4,058,367 | 11/1977 | Gilford | 422/67 X |
| 4,158,545 | 6/1979 | Yamashita et al. | 23/230 R |

*Primary Examiner*—Ronald Serwin

*Attorney, Agent, or Firm*—Craig and Antonelli

[57] ABSTRACT

A train of cuvettes are held on a turntable and serum specimen is sequentially sampled each time the turntable makes a revolution through more than 360°. While the turntable is at rest, blank solution is poured into one cuvette, reagent is put into another cuvette and reactant solution is drawn out of still another cuvette in specified positions respectively in the path along which the train of cuvettes are conveyed. During a single rotational operation of the turntable, these cuvettes sequentially transverses the light path in the photometer so that the light absorbances for the respective cuvettes are measured. Both the absorbances for cuvettes containing reactant solutions for different samples and the absorbance for a cuvette containing only the blank solution are measured by a single photometer. The difference between the value of measurement obtained from a specified cuvette filled with reactant solution and the value of measurement obtained from the same cuvette filled with blank solution alone, is calculated and an analyzed value corrected is obtained for any desired analysis item in accordance with the calculated difference.

6 Claims, 5 Drawing Figures

AUTOMATIC CHEMICAL ANALYZING METHOD AND APPARATUS

BACKGROUND OF THE INVENTION

This invention relates to an automatic chemical analyzing method and apparatus and more particularly to an analyzing method and apparatus in which a liquid sample and a reagent are successively poured into a plurality of cuvettes conveyed discretely, the optical characteristics of the reacting solutions in the cuvettes being automatically measured.

According to most conventional chemical analyzing methods used especially in hospitals for clinical examination, a certain quantity of a sample to be measured is put in a reaction vessel or a cuvette and reagent is added to the sample so as to cause a chemical reaction to take place, colorimetric measurement or rate assay measurement is performed by using a spectrophotometer, and the concentrations of the constituents or other factors in any specified unit are derived as an analyzed result from the result of the previous measurement. Examples of such an analyzing method are U.S. Pat. No. 4,025,311 where a reaction chamber is used, and U.S. Pat. No. 4,158,545 where conveyed cuvettes are employed.

In an automatic chemical analyzing apparatus including the above examples, which performs the measurement operations automatically, it is customary for each measurement cell or cuvette to be used repeatedly. In such a case, even if each cuvette is cleaned every time after use by way of the cleaning operation comprising part of the analyzing process, fatty components contained in the sample will gradually increase the opacity of the cuvettes light-permeable surface and such opacity will contribute to measurement error. Also, flaws in the light-permeable surface of the cuvette will lead to measurement error. Further, since the photometers output causes zero drift phenomenon due to fluctuation of the luminosity of the light source and changes in the characteristics of the optical system, the detectors and the electric circuitry, the measured value adversely fluctuates with the lapse of time so that the difference between the initially measured value for the blank and the measured value fluctuates.

SUMMARY OF THE INVENTION

One object of this invention is to provide a method for improving precision in the analysis of reactant solution with an automatic chemical analyzing apparatus having a plurality of cuvettes.

Another object of this invention is to provide an analyzing method and apparatus which are capable of obtaining analyzed values corrected with respect to the opacity of cuvettes which varies with time.

Yet another purpose of this invention is to provide an analyzing method and apparatus capable of measuring the blank value of each one of a train of cuvettes provided for a group of samples.

Still another purpose of this invention is to provide an analyzing method and apparatus which are capable of measuring the optical property of one reactant solution and the blank value of another simultaneously by a single photometer.

An additional object of this invention is to provide an analyzing method and apparatus which can measure the reactant solutions in the cuvettes while correcting errors arising from opaque regions of the cuvettes and the zero drift of the photometer.

The automatic chemical analyzing method of this invention comprises:

a step of conveying a cuvette containing a reactant solution consisting of a sample and a reagent and measuring the light passing through the cuvette which is caused to traverse the light path in the photometer during conveyance;

a step of storing as the first measured value the value obtained by measuring the light which was passed through the cuvette containing the reactant solution;

a step of pouring a blank solution into an empty cuvette;

a step of conveying the cuvette filled with the blank solution and measuring the light through the cuvette filled with the blank solution by causing the cuvette to traverse the light path in the photometer during conveyance;

a step of storing as the second measured value the value obtained by measuring the light which has passed through the cuvette filled with the blank solution; and a step of displaying the concentrations of components to be analyzed in the sample, in accordance with the magnitude of the difference between the first and second measured values.

The automatic chemical analyzing apparatus comprises:

a holding means for holding a train of light-permeable cuvettes;

a conveying means for conveying a sample cup containing a liquid sample to the intake position;

a step of taking the sample out of the sample cup resting in the intake position and placing the removed sample into the cuvette held by the holding means;

a light measuring means for casting light upon the cuvette and detecting the light after it has passed through the cuvette;

a driving means for driving the holding means in such a manner that the first and second operations are performed sequentially, the first operation conveying the cuvette from the starting position on the holding means and the second operation causing the conveyed cuvette to traverse the light path in the light measuring means and then stopping the conveyed cuvette in a position ahead of the starting position;

a means for adding a reagent into a cuvette at a specified position while the train of cuvettes is stationary;

a control means for obtaining the second measured value of a cuvette by the light measuring means when the cuvette contains a reactant solution consisting of sample and reagent and for storing the obtained second measured value in a memory section, and also for obtaining the first measured value of the cuvette by the light measuring means when it contains a solution in which at least one of the sample and the reagent are not present and for storing the obtained first measured value in the memory section; and a displaying means for displaying the concentrations of the components to be analyzed in the sample, in accordance with the difference between the first and second measured values.

DESCRIPTION OF THE PREFERRED EMBODIMENT

Figure 1:
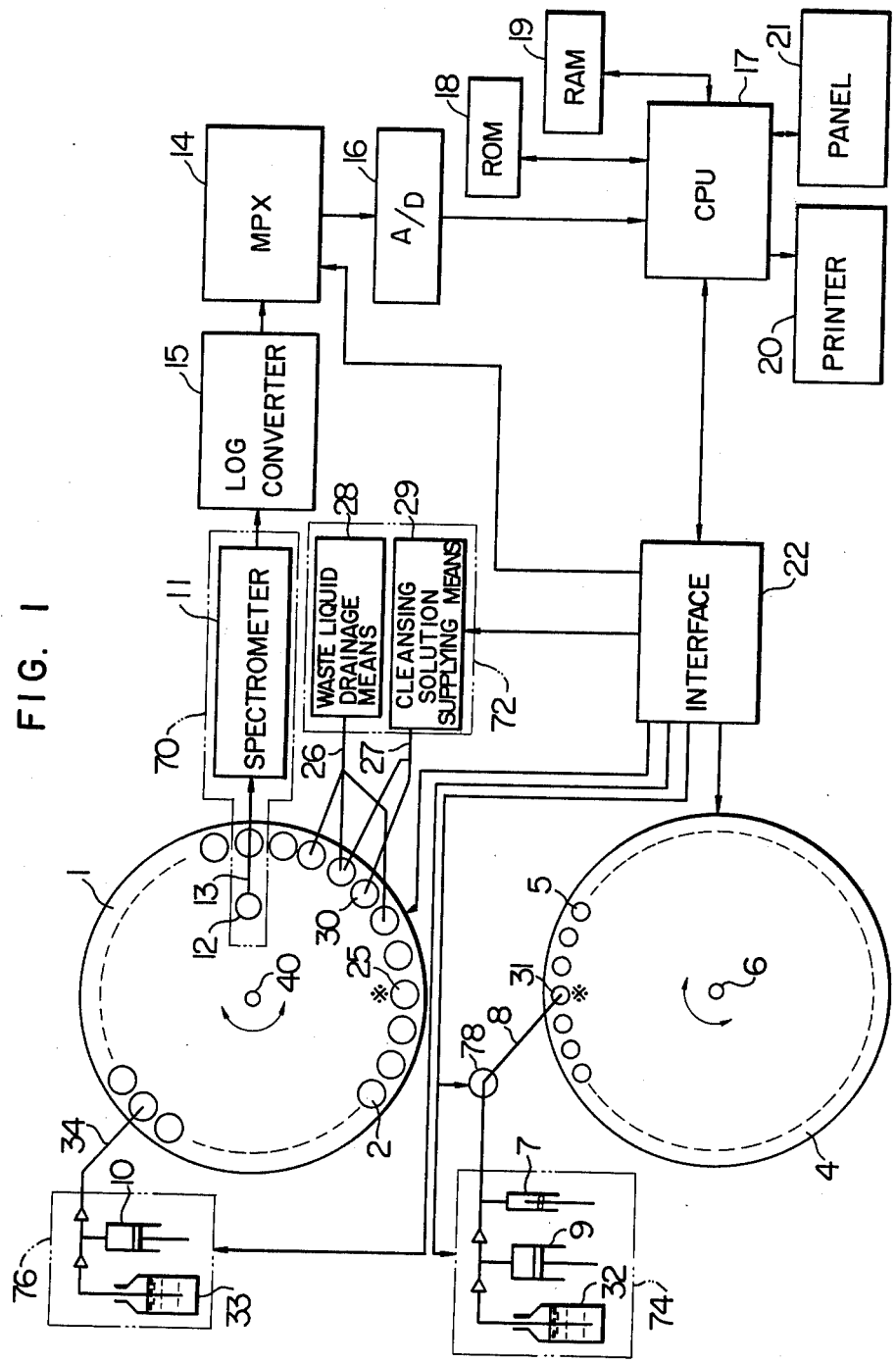
FIG. 1 shows a schematic structure of an embodiment of this invention.

FIG. 1 schematically shows an automatic chemical analyzing apparatus as an embodiment of this invention. Reaction turntable 1 can be rotated on rotary shaft 40 in either the forward or backward direction. A plurality of, e.g. forty, of cuvettes 2 are held on the periphery of reaction turntable 1. Sample turntable 4 can be rotated on rotary shaft 6 in either the forward or backward direction. A plurality of sample cups 5, each containing a liquid sample such as, for example, blood serum are held on the periphery of sample turntable 4.

The sampling operation is performed by a distributor 74 which comprises a sampling probe 8 and probe shifter 78. The probe shifter 78 can horizontally shift the sampling probe 8 tipped with a nozzle from intake position 31 to ejection position 25 and also vertically shift the probe 8 in both intake and ejection positions 31 and 25. Distributor 74 also comprises a microsyringe 7 for taking in the sample, a syringe 9 for supplying the sample and a first vessel 32 for liquid samples.

A reagent supplier 76 comprises a length of pipe 34 extended to the train of cuvettes held by reaction turntable 1, a syringe 10 for supplying reagent and a second vessel 33 for liquid reagent. The supply of reagent for the cuvettes in the reaction turntable 1 is performed by both the distributor 74 and reagent supplier 76, but for the component or analysis item which requires only one kind of reagent for analysis, distributor 74 alone is used. The number of distributors 74 to be used is equal to the number of the components or items to be analyzed. The number of reagent suppliers 76 to be used is equal to the number of the analysis items each of which requires two kinds of reagent for analysis.

Figure 2:
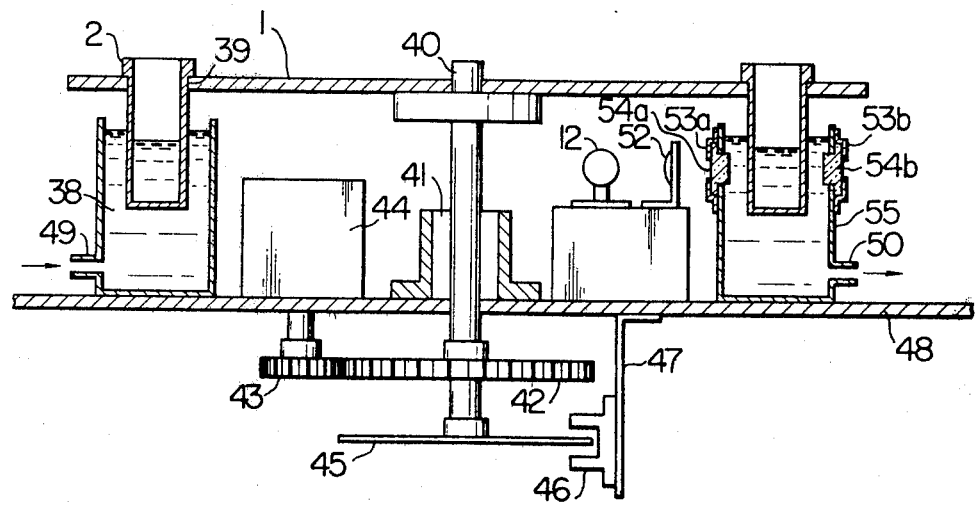
FIG. 2 is a partial cross-section of a reaction turntable with its peripheral equipment, as an embodiment of this invention.

A drive means for driving the reaction turntable 1 is constructed as shown in FIG. 2. Rotary shaft 40 of turntable 1 is supported by a bearing 41 and disc 45 for position detection is attached to the end of shaft 40 at the extreme position from turntable 1. A cogged wheel 42 fixed to rotary shaft 40 is engages with cogged wheel 43 attached to the drive shaft of a pulse motor 44. Bearing 41 and a pulse motor 44 are rigidly mounted on a base 48. A photointerrupter 46 has a light source and a light receiving element installed opposite to each other in such a manner that disc 45 rotates horizontally between the light source and the light receiving element. Photointerrupter 46 is rigidly supported on a metal bracket 47 fixed to base 48. Perforations in the disc 45 allow light to pass through, along a concentric path with predetermined radii. Each time the perforations pass by the photointerrupter 46, a detection signal is received. The number of perforations on disc 45 for passing light through is equal to the number of holes 39 cut in the reaction turntable 1 for stably receiving the cuvettes. Also, the angle subtended by the centers of the two adjacent holes 39 with respect to the center of turntable 1 is also equal to the corresponding angle on disc 45. Pulse motor 44 is connected through an interface 22 shown in FIG. 1, with a central processing unit (CPU) 17. In this embodiment, disc 45 has 40 perforations corresponding to the number of cuvettes 2 to be employed for analysis. CPU 17 sends a rotation starting signal to motor 44. As disc 45 rotates, the photointerrupter 46 delivers detection signals, the number of which corresponds to the perforations which have traversed photointerrupter 46. CPU 17 causes the motor 44 to stop when the number of detection signals delivered exceeds a predetermined number which is greater than the number of perforations on disc 45, for example, when forty-one detection signals are delivered. In this case, turntable 1 also makes more than one revolution.

Figure 3:
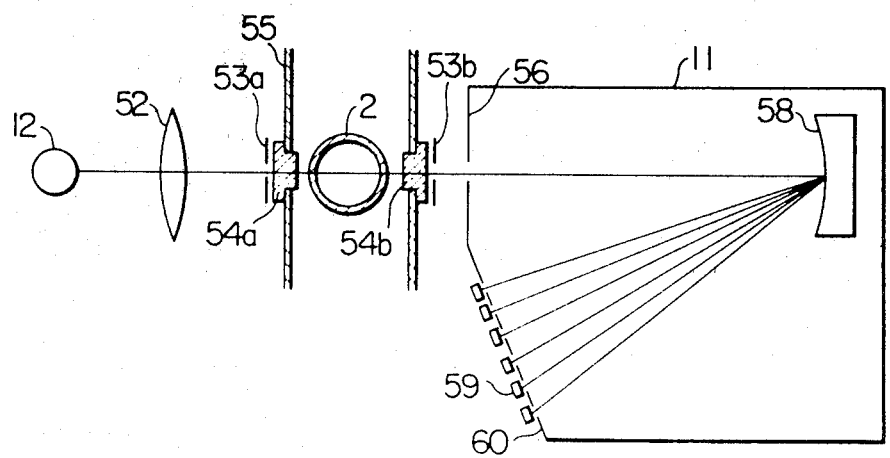
FIG. 3 schematically shows a light measuring apparatus with its peripheral equipment, as an embodiment of this invention.

The light measuring apparatus, photometer 70 in FIG. 1, comprises a lamp 12 as a light source and a spectrometer 11. Photometer 70 is shown in greater detail in FIGS. 2 and 3. A light beam 13 travelling from light source 12 to spectrometer 11 traverses the path along which the train of cuvettes is conveyed. Under reaction turntable 1 is an annuler-shaped constant temperature bath 55 which is filled with water 38 kept at a constant temperature. Since the curvature of the annular-shaped bath 55 coincides with the circle along which the train of cuvettes is arranged, all the cuvettes have their lower portions submerged in the constant temperature water 38 of bath 55 during conveyance. Transparent windows 54a and 54b and slits 53a and 53b are provided in the desired areas of the side walls of bath 55. The constant temperature water 38 flows into bath 55 through an entrance 49 and out through an exit 50. The light emitted from source 12 is concentrated into a beam 13 and the beam 13 is led to spectrometer 11 through a lens 52, transparent windows 54a and 54b, and an entrance slit 56. The beam guided into the spectrometer 11 is broken down into different wavelength components by means of a concave grating 58 and the respective components are detected by semiconductor photodetectors 59 suitably arranged in accordance with the wavelengths to be detected. The diameter of the beam spot projected on each of the photodetectors 59 is determined by the dimensions of an exit slit 60. Each cuvette 2 supported on turntable 1 and conveyed along a circular path is made to traverse the beam 13 in the photometer during its circular movement. Since beam 13 is made to pass through the cuvette 2 and the liquid contained therein, the total absorption of light, that is, the absorption by the cuvette 2 plus the absorption by the liquid therein, can be detected. The beam path is so positioned that when turntable 1 is stationary, the beam 13 passes through the center of the cuvette 2 which, for example, may be the thirtieth cuvette counted clockwise from ejection position 25. The respective photodetectors 59 are connected with corresponding logarithmic amplifiers 15, each of which is connected with two multiplexers 14. Each of the two multiplexers 14 extracts a photo-signal corresponding to a single wavelength. The two signals corresponding to the two wavelengths extracted by the two multiplexers are respectively digitalized by an A/D converter 16 and the digital signals are received by the CPU 17.

Figure 4:
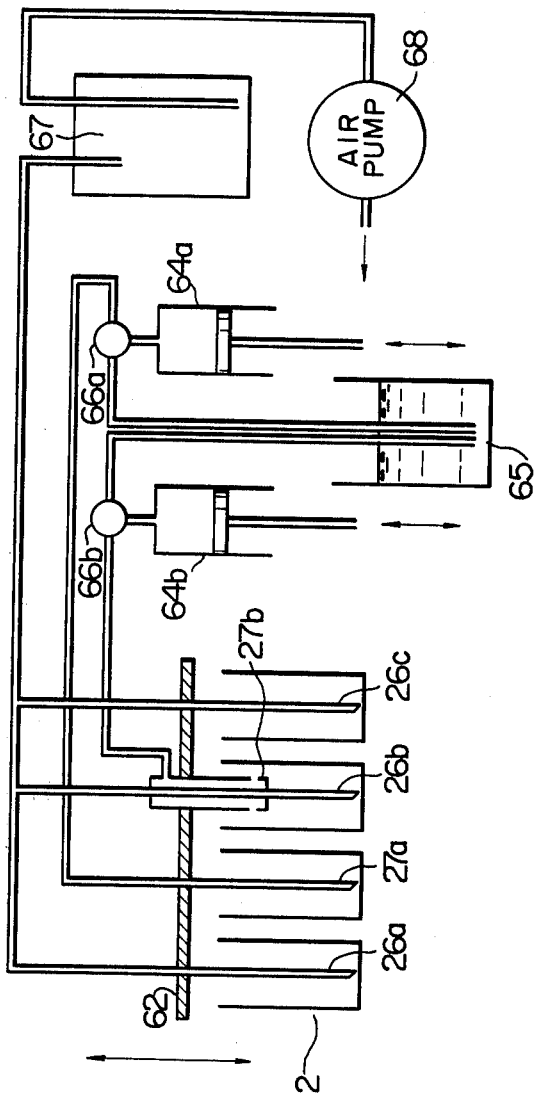
FIG. 4 schematically shows a cleansing apparatus with its peripheral equipment, as an embodiment of this invention.

A waste liquid drainage pipe 26 and a cleansing solution supply pipe 27 are provided between the sample ejection position and the position of intersection between the light beam 13 and the path of the train of cuvettes. A cleansing apparatus 72 comprises a waste liquid drainage means 29 to which drainage pipe 26 is connected and a cleansing solution supplying means 29 to which supply pipe 27 is linked. Cleansing apparatus 72 is shown in greater detail in FIG. 4. Drainage pipes 26a, 26b and 26c are connected to a waste liquid tank 67 and the waste liquid in tank 67 is drained off by an air pump 68. A cleansing solution supply pipe 27a is linked with a tank 65 containing distilled water via the three-way electromagnetic valve 66a of a syringe 64a. A cleansing solution supply pipe 27b is linked with tank 65 via the three-way electromagnetic valve 66b of a syringe 64b. The waste liquid drainage pipe 26 and the cleansing solution supply pipe 27 are supported by a support member 62 which is shifted up and down by a mechanism not shown. FIG. 4 shows the state where waste liquid drainage pipe 26 and cleansing solution supply pipe 27 are shifted down into the cuvettes located at predetermined positions when turntable 1 is stopped.

CPU 17 in FIG. 1 is connected through a bus line with the interface 22, A/D converter 16, a read-only memory (or ROM) 18, a random-access memory (or RAM) 19, a manipulation panel 21 and a printer 20.

When sample cup 5 containing a serum sample is sent to sampling position 31 on sample turntable 4, the tip of the sampling probe 8 is immersed in the liquid in the sample cup 5 so that a quantity of serum is sucked up and held in the probe 8. At the same time, syringe 9 sucks up a first reaction reagent from the reagent vessel 32. Probe 8 is then shifted to ejection position 25 and the serum held in the probe 8 is ejected into the cuvette 2 resting at the ejection position while the syringe 9 ejects the specified quantity of the first reaction reagent into the same cuvette. As a result, the sample is mixed with the first reaction reagent in the cuvette so that the first reaction takes place. After the completion of the above sampling operation, reaction table 1 starts rotating clockwise and rotates through 369 degrees which corresponds to the angle through which 41 cuvettes, that is, cuvettes whose number is greater by one than that of all the cuvettes held on turntable 1, pass through the ejection position 25.

After the above rotational operation, the cuvette 2 containing the apportioned sample and the first reaction reagent is located at the position in advance by one pitch, i.e. 9 degrees, clockwise of the ejection position 25. During one revolution of turntable 1, all the cuvettes 2 on turntable 1 traverse light beam 13. Accordingly, when each cuvette 2 crosses the beam 13, the spectrometer 11 performs absorbance measurement. The output of spectrometer 11 is sent through the logarithmic amplifier 15 to the multiplexer 14, which selects the signal having a desired wavelength. The output of multiplexer 14 is sent through the A/D converter 16 to the CPU 17 for storage in the RAM 19. The above series of operations is repeated every thirty seconds, provided that a cycle consisting of the time for which turntable 1 is moving and the time for which it is stationary, is set equal to 30 sec. As the cycles advance, a particular sample advances, pitch by pitch, clockwise.

A tube 34 for adding the second reagent to the sample is located at the fifteenth cuvette counted clockwise from ejection position 25. Accordingly, and particular sample initially resting at the ejection position 25 and undergoing the first reaction there, will receive the second reagent to initiate the second reaction in the fifteenth cycle. If there is no need for a second reaction, the second reagent is not added. The samples in the cuvettes located between beam 13 and ejection position 25 have already been measured and therefore are sucked out through drainage tube 26 by a waste liquid drainage means 28. Cleansing solution is then supplied to the evacuated cuvette through the cleansing solution supplying tube 27 from the cleansing solution supplying means 29. The cuvette 2 filled with cleansing solution (usually distilled water) at the position where the last supply of cleansing solution takes place, traverses light beam 13 during the next rotation of turntable 1 so that the light absorbance indicating the blank value of the cuvette is measured and the result of the measurement is temporarily stored in the RAM 19. When the cuvette 2 next comes to rest, the cleansing solution is sucked out as described above. This is the last draining operation performed on the particular cuvette 2. In the succeeding cycle, this cuvette 2 is used as a renewed cuvette at the ejection position.

The preceding operations are effected through the control of the respective mechanisms by the CPU 17 via the interface 22 in accordance with the program stored in ROM 18. The operation panel 21 is used to supply measurement conditions and to start and stop measurement.

If the above defined cycle is set so that the resting time is 9.5 sec and the rotating time 20.5 sec, thirty measurements of the reaction process will be performed on any particular sample every 29.5 sec and the total data measured for 14 minutes and 45 seconds is stored in the RAM 19. CPU 17 operates on the program in ROM 18 and checks the thirty items of measurement data in RAM 19. When no abnormality is found in the reaction process, the blank value previously stored as reference for light absorption measurement in RAM 19 is subtracted from the last item of data or the data obtained through statistical processing such as, averaging of several successive items of data. The difference thus obtained is converted to the unit to be delivered as output and then displayed on the printer 20. For analysis by the reaction rate measurement method, the variation in the absorbance per unit time is calculated from the data obtained after the start of the second reaction. The calculated result is multiplied by an output unit conversion factor and then printed out by the printer 20. The above used blank value is obtained for each cuvette for each use in a cycle.

Figure 5:
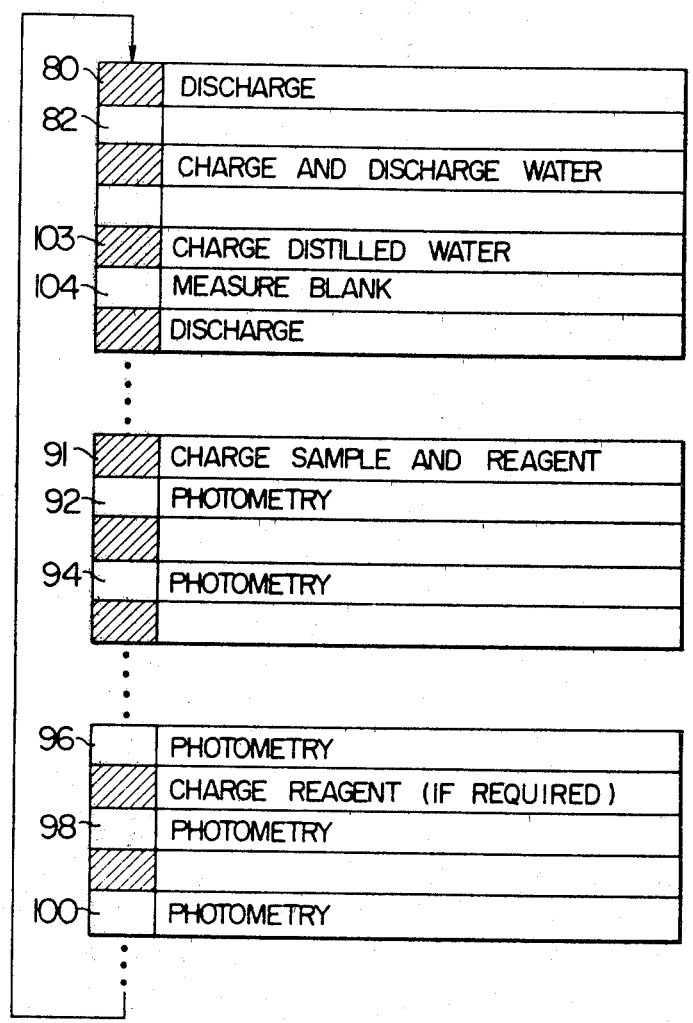
FIG. 5 shows a series of steps of an operation performed with a single cuvette.

FIG. 5 is the tabulation of the above described series of measurement operations, illustrating analytical measurement performed with a single cuvette. In FIG. 5, the cross-hatched portion 80 indicates the state of the turntable while stationary and the blank portion 82 shows the state of turntable 1 when stationary.

In stationary state 91, sample and reagent are supplied to cuvette 2 at the ejection position, to produce a reactant solution. In the rotating states 92, 94, 96, 98 and 100 following state 91, the cuvette containing reactant solution is so conveyed as to traverse the light beam 13 in light measuring apparatus 70 and the absorbance of the cuvette containing the reactant solution is measured and stored as the first measured value in RAM 19. In stationary state 80, the reactant solution in the cuvette is drawn out by means of drainage tube 26. In stationary state 103, distilled water as blank solution is supplied to the cuvette through supply tube 27b. In the rotating state 104, the cuvette containing the blank solution is so conveyed as to traverse light beam 13 in the light measuring apparatus 70. Then, the absorbance of the cuvette filled with the blank solution is measured and stored as the second measured value in RAM 19. The concentration of any desired component in the sample is calculated in accordance with the first and second measured values stored in RAM 19 and the calculated result is displayed on the printer 20.

As is apparent from the descriptions of FIGS. 1 and 5, while a particular cuvette is stationary for reception of reaction reagent, blank solution is poured into other cuvette which are also stationary. Then, the particular cuvette and the other cuvettes are moved together to traverse light beam 13 in light measuring apparatus 70.

As described above, according to the embodiment of this invention, since the blank values used as references for the measurement of light absorbance are obtained for the respective cuvettes 2 each time before use after cleansing, the particular absorbance characteristics of the cuvettes 2 inclusive of long-term fluctuations can be corrected precisely.

Further, errors due to zero drift in the optical and electrical systems can also be eliminated by subtracting the blank value (reference value) from the measured one.

Moreover, according to this embodiment, if the measured blank value of a cleansing cuvette 2 is abnormal, that is, it exceeds a preset allowable limit, then the cuvette is regarded as having flaws on its light-permeable surfaces or as not being sufficiently cleanse so that a warning mark is attached to the measurement result of the sample in question or an alarm is issued or that the following operations of receiving samples into cuvettes are interrupted. Accordingly, any possibility of a harmful result arising from measurement error can be minimized.

With this invention, since the blank value of a cuvette is measured while the cuvette is filled with distilled water used as cleansing solution, the influence on measurement due to the lens effect of the cuvette surfaces and to flaws of the inner surfaces of the cuvette can be eliminated so that the measured blank value approximates the blank value of a cuvette containing an actual sample. Moreover, in the case where the above influences are negligible, the blank value may be measured by using an empty cuvette.

According to this embodiment, since the turntable holding the cuvettes makes many revolutions intermittently, there is no need for a separate spectrometer especially for measuring blank values during revolution.

The preceding description exclusively concerns the case where this invention is applied to an automatic chemical analyzing apparatus in which each cuvette serving as a measurement cell is repeatedly re-used after cleansing operation, but the invention is not limited to this embodiment. For example, this invention can also be applied to a method whereby each cuvette is discarded after single use, to be replaced by a new one, if the blank value of the new cuvette is measured before sample measurement.

Furthermore, the embodiment described above is an application of this invention to an automatic chemical analyzing apparatus wherein cuvettes are held on a turntable and moved as the turntable revolves. However, this invention is by no means limited to this structure, but may be suitably applied to an automatic chemical analyzing apparatus wherein cuvettes are conveyed on an endless belt.

We claim:

1. An automatic chemical analyzing method comprising
   a step of putting a sample and a reagent into at least specified one of a train of cuvettes to produce a reactant solution, said train of cuvettes being conveyed along a circular path;
   a step of conveying said train of cuvettes along said circular path each time reagent is added to a sample, and of causing all of said cuvettes to traverse the light beam in the light measuring apparatus placed in said circular path;
   a step of storing as a first measured value the value obtained by measuring the light having passed through said specified cuvette filled with said reactant solution;
   a step of draining said reactant solution out of said specified cuvette;
   a step of pouring blank solution into said specified cuvette which was previously emptied during the period for which said specified cuvette is at rest;
   a step of producing reactant solution in at least one of said cuvettes other than said specified cuvette during said period of said specified cuvette being at rest;
   a step of conveying said train of cuvettes along said circular path each time blank solution is added, so that all the cuvettes may be caused to traverse said light path;
   a step of storing as a second measured value the value obtained by measuring the light having passed through said specified cuvette filled with said blank solution; and
   a step of displaying the concentration of any analysis item in said sample in accordance with the magnitude of the difference between said first and second measured values.

2. A method as claimed in claim 1, wherein a cuvette resting at the position where reagent is added is conveyed across said light measuring apparatus and brought to a halt at a point ahead of said position where reagent is added.

3. An automatic chemical analyzing apparatus comprising
   a holding means for holding a train of cuvettes each permeable to light;
   a means for sending a sample cup containing a liquid sample to the intake position;
   a means for transferring said liquid sample from said sample cup in said intake position to any cuvette held by said holding means;
   a light measuring means for applying light to any cuvette and measuring the light having passed through the cuvette;
   a driving means for driving said holding means in such a manner that a first and a second operations are sequentially performed, said first operation starting to convey a cuvette at rest at the starting point on said holding means and said second operation bringing said cuvette to a halt in the position ahead of said starting point after said cuvette has traversed the light path in said light measuring apparatus;
   a means for adding reagent to a cuvette located at a specific position while said train of cuvettes are at rest;
   a control means for obtaining a first measured value from a cuvette by said light measuring apparatus and storing said first measured value in a memory when said cuvette does not contain at least one of sample and reagent, and for obtaining a second measured value from said cuvette by said apparatus and storing said second measured value in said memory when said cuvette contains both sample and reagent; and a display means for displaying the concentration of any analysis item in accordance with the difference between said first and second measured values.

4. An automatic chemical analyzing apparatus as claimed in claim 3, further comprising a cleansing means for pouring cleansing solution into the cuvette which has been emptied of its reactant solution and also for drawing said cleansing solution out of said cuvette.

5. An automatic chemical analyzing apparatus comprising a holding means for holding a train of cuvettes each permeable to light;

a means for sending a sample cup containing a liquid sample to the intake position;

a means for transferring said liquid sample from said sample cup in said intake position to any cuvette held by said holding means;

a light measuring means for casting light upon any cuvette and measuring the light having passed through the cuvette;

a driving means for driving said holding means in such a manner that a first and a second operations are sequentially performed, said first operation starting to convey a cuvette at rest at the starting point and said holding means and said second operation bringing said cuvette to a halt in the position ahead of said starting point after said cuvette has traversed the light path in said light measuring apparatus;

a means for adding reagent to a cuvette located at a specified position while said train of cuvettes are at rest;

a means for pouring blank solution into said cuvette;

a control means for obtaining a first measured value from a cuvette by said light measuring apparatus and storing said first measured value in a memory when said cuvette contains only said blank solution, and for obtaining a second measured value from said cuvette by said apparatus and storing said second measured value in said memory when said cuvette contains both sample and reagent; and a display means for displaying the concentration of any analysis item in accordance with the difference between said first and second measured values.

6. An automatic chemical analyzing apparatus comprising a turntable for holding a train of cuvettes each permeable to light;

a means for sending a sample cup containing a liquid sample to the intake position;

a means for transferring the sample from said sample cup in said intake position to any of said cuvettes held by said turntable;

a light measuring means for casting light upon a cuvette and measuring the light having passed through said cuvette;

a disc disposed coaxial with the rotary shaft of said turntable, having perforations corresponding to said cuvettes held by said turntable;

a position detecting means having a light source and a light receiving element disposed on both sides of the peripheral portion of said disc;

a driving means for rotating said turntable in response to every rotation instruction signal until said position detecting means detects a predetermined number of said perforations, said predetermined number being greater than the number of said perforations cut in said disc, a means for putting reagent into a cuvette in a specified position while said train of cuvettes are at rest;

a control means for detaining a first measured value from a cuvette by said light measuring apparatus and storing said first measured value in a memory when said cuvette does not contain at least one of sample and reagent, and for obtaining a second measured value from said cuvette by said apparatus and storing said second measured value in said memory when said cuvette contains both sample and reagent, said control means delivering said rotation instruction signal to said driving means; and a display means for displaying the concentration of any analysis item in accordance with the difference between said first and second measured values.

* * * * *